(12) United States Patent
Mehdizadeh et al.

(10) Patent No.: US 7,877,869 B2
(45) Date of Patent: Feb. 1, 2011

(54) LEAD BODY-TO-CONNECTOR TRANSITION ZONE

(75) Inventors: Bruce R. Mehdizadeh, Savage, MN (US); Sandra F. Viktora, Coon Rapids, MN (US); Catherine A. Lundberg, Blaine, MN (US); Dina L. Williams, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 24 days.

(21) Appl. No.: 12/124,348

(22) Filed: May 21, 2008

(65) Prior Publication Data

US 2008/0244903 A1    Oct. 9, 2008

Related U.S. Application Data

(62) Division of application No. 10/922,210, filed on Aug. 19, 2004, now Pat. No. 7,395,116.

(51) Int. Cl.
*H05K 3/00*    (2006.01)

(52) U.S. Cl. ............ 29/842; 29/883; 29/592.1; 607/126; 607/122; 607/37; 607/148; 600/373

(58) Field of Classification Search ............ 29/883, 29/592.1; 607/126, 122, 37, 148; 600/373
See application file for complete search history.

(56) References Cited

U.S. PATENT DOCUMENTS

| 5,303,704 | A | | 4/1994 | Molacek |
| 5,483,022 | A | | 1/1996 | Mar |
| 5,584,873 | A | | 12/1996 | Shoberg |
| 5,715,817 | A | | 2/1998 | Stevens-Wright |
| 5,800,496 | A | | 9/1998 | Swoyer |
| 5,935,159 | A | * | 8/1999 | Cross et al. ............ 607/116 |
| 6,249,708 | B1 | * | 6/2001 | Nelson et al. ............ 607/122 |
| 6,556,873 | B1 | | 4/2003 | Smits |
| 6,999,821 | B2 | | 2/2006 | Jenney |
| 2003/0139794 | A1 | | 7/2003 | Jenney |
| 2004/0039434 | A1 | | 2/2004 | Schrom |

FOREIGN PATENT DOCUMENTS

EP    1023915 A    8/2000

OTHER PUBLICATIONS

International Search Report, PCT/US2005/028395, May 26, 2006, 6 Pages.

* cited by examiner

*Primary Examiner*—A. Dexter Tugbang
*Assistant Examiner*—Azm Parvez
(74) *Attorney, Agent, or Firm*—Reed A. Duthler (57) ABSTRACT

A medical electrical lead includes a lead body and a connector terminal. A conductor extends from the lead body to the connector terminal along a helical path through a transition zone.

31 Claims, 6 Drawing Sheets

LEAD BODY-TO-CONNECTOR TRANSITION ZONE

CROSS REFERENCE TO PRIORITY APPLICATION

This application is a divisional of U.S. application Ser. No. 10/922,210, filed Aug. 19, 2004, now U.S. Pat. No. 7,395,116 which is incorporated herein by reference.

TECHNICAL FIELD

The present invention relates to medical electrical leads and more particularly to lead body-to-connector terminal transition zones.

BACKGROUND

A host of medical devices include a connector bore into which a connector terminal of an electrical lead, or catheter, is inserted in order to make electrical connection with the device so as to form a medical system. Each insulated conductor, extending within a body of the lead, couples a lead electrode and or other electrically activated sensor to an electrical contact element formed on the connector terminal, and each contact element is engaged by a contact within the device connector bore when the connector is fully inserted within the bore. When the connector terminal of a lead is thus coupled to a device and the resulting system implanted within a body of a patient, certain stresses and strains may develop in a transition zone between the body of the lead and the connector terminal; these stresses and strains may lead to conductor failures within the transition zone. Thus, a transition zone designed to mitigate such stresses and strains is needed.

BRIEF DESCRIPTION OF THE DRAWINGS

The following drawings are illustrative of particular embodiments of the invention and therefore do not limit its scope, but are presented to assist in providing a proper understanding of the invention. The drawings are not to scale (unless so stated) and are intended for use in conjunction with the explanations in the following detailed description. The present invention will hereinafter be described in conjunction with the appended drawings, wherein like numerals denote like elements, and:

FIGS. 3A-8 are a perspective view and schematic, respectively, of another multi-lumen tube according to some embodiments of the present invention;

DETAILED DESCRIPTION

The following detailed description is exemplary in nature and is not intended to limit the scope, applicability, or configuration of the invention in any way. Rather, the following description provides a practical illustration for implementing exemplary embodiments of the invention.

Figure 1:
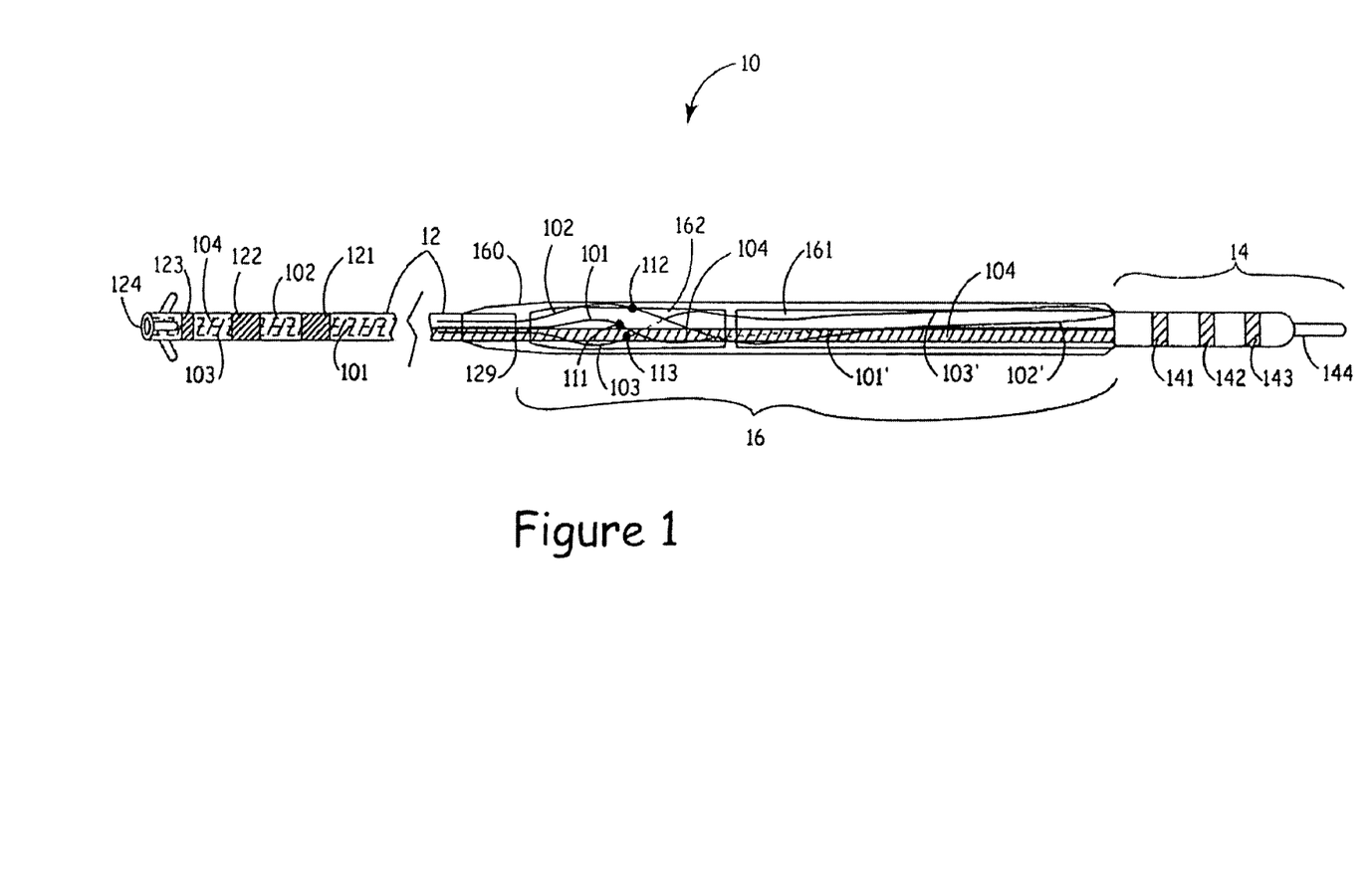
FIG. 1 is a plan view of an exemplary medical lead including an embodiment of the present invention.

FIG. 1 is a plan view of an exemplary medical lead 10 including an embodiment of the present invention. FIG. 1 illustrates lead 10 including a lead body 12 and a lead connector terminal 14 joined to lead body 12 in a transition zone 16 that extends between a proximal end 129 of body 12 and connector terminal 14; a plurality of electrodes 121, 122, 123 and 124 coupled to a distal portion of body 12 are electrically coupled to corresponding connector contacts 141, 142, 143 and 144, respectively, via elongate conductors 101/101', 102/102', 103/103' and 104. According to the illustrated embodiment, lead body 12 includes a multi-lumen tubing through which conductors 101, 102, 103 and 104 extend; conductors 101, 102, 103 and 104 exit from proximal end 129 to meet with corresponding conductors 101', 102' and 103' in transition zone 16 where ends of each are spliced together at junctions 111, 112 and 113, respectively. Conductors 101/101', 102/102', 103/103' may be in the form of cables and conductor 104 in the form of a coil; such cabled and coiled conductor configurations may be formed of one or more conductor wires made of MP35N alloy according to configurations well known to those skilled in the art. It should be noted that embodiments of the present invention also include those without splice junctions 111, 112 and 113 wherein conductors are continuous from lead body 12 to connector 14.

FIG. 1 further illustrates transition zone 16 contained within a connector sleeve 160 and including a first multi-lumen tube 161, positioned adjacent connector 14, and a second multi-lumen tube 162, positioned adjacent proximal end 129 of lead body 12; each lumen of first second multi-lumen tubes 161 and 162 serves to route each one of conductors 101/101', 102/102', 103/103' and 104 from lead body 12 to connector 14. According to embodiments of the present invention, conductors 101/101', 102/102' and 103/103' are routed in a helical path within transition zone 16 so that stresses and strains may be alleviated. Although FIG. 1 illustrates transition zone 16 including two tubes 161 and 162, alternate embodiments of the present invention can employ a single tube within zone 16 to provide the helical routing. According to some of these alternate single tube embodiments, helical routing has a constant pitch along a length of transition zone 16, while according to others of these embodiments helical routing has a variable pitch along a length of transition zone 16, for example as illustrated in FIG. 1

Figure 2A:
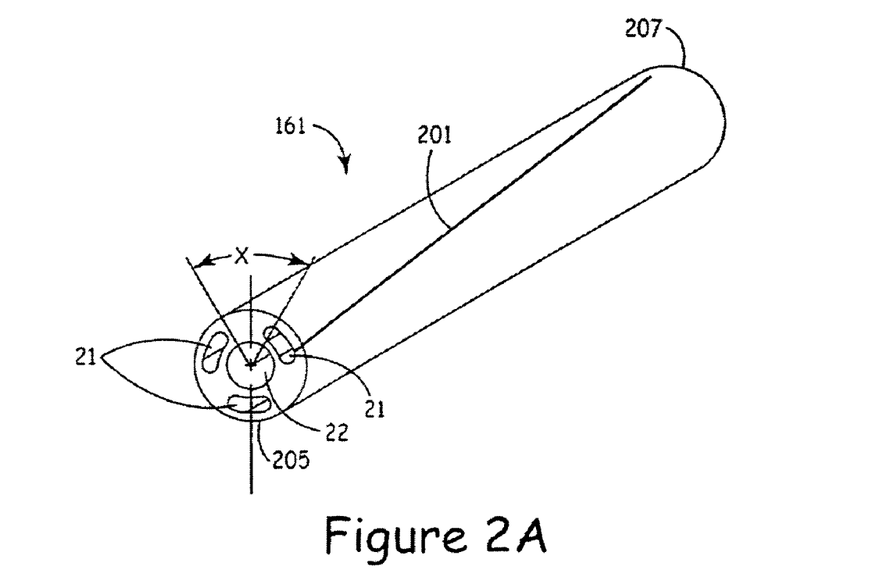
FIGS. 2A-B are a perspective view and a schematic, respectively, of a multi-lumen tube according to some embodiments of the present invention.
Figure 2B:
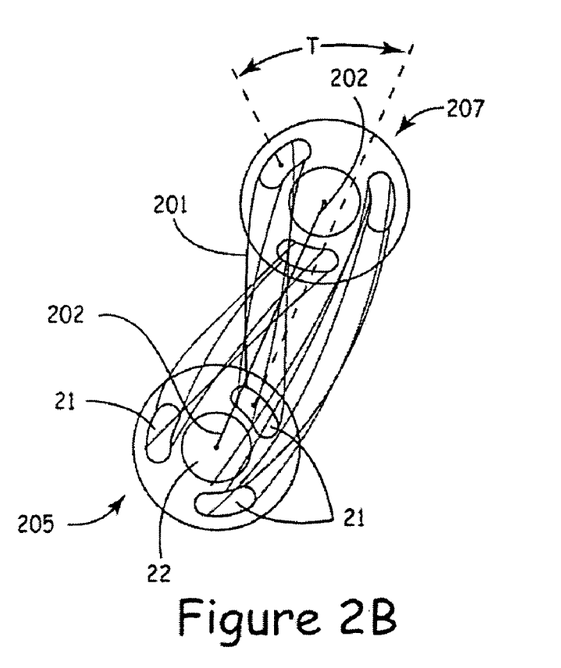

FIGS. 2A-B are a perspective view and a schematic, respectively, of multi-lumen tube 161 according to some embodiments of the present invention. FIGS. 2A-B illustrate tube 161 including a central lumen 22 and three peripheral lumens 21 each extending from a first end 205 to a second end 207 of tube 161; peripheral lumens 21 each extend along a helical path about central lumen 22, for example as illustrated by a bold line 201. According to the illustrated embodiment, peripheral lumens 21 twist about central lumen 22 from first end 205 to second end 207 in an angle T, which is approximately 90 degrees, but may be as great as approximately 180 degrees; thus, a pitch of the helical path of lumens 21 is greater than a length of tube 161 from first end 205 to second end 207, which length is between approximately 1.25 inches and 1.5 inches.

FIGS. 2A-B further illustrate lumens 21 each having a ellipsoid cross-section and offset about a periphery of central lumen 22 at an angle X between adjacent edges of lumens, angle X being approximately 45 degrees according to the illustrated embodiment. According to one embodiment of the present invention, the ellipsoid cross-section of lumens 21 provides a loose fit of conductors 101', 102' and 103', having a generally circular cross-section, therein, thus allowing movement of the conductors for stress relief and further providing some slack so that an orientation of first multi-lumen tube 161 with respect to second multi-lumen tube 162 is not as critical.

According to an exemplary embodiment of the present invention, first multi-lumen tube 161 is made of polyurethane; tube 161 would have been extruded so that a center axis of lumens 21 is approximately straight extending parallel to a central axis of central lumen 22 and then taken through a secondary process to create the twisted configuration illustrated in FIGS. 2A-B. The secondary process, according to one embodiment, includes clamping first end 205 to a fixture plate and then rotating or twisting, through angle T, second end 207 with respect to first end 205; second end 207 is then secured or clamped to the plate and tube 161 is held at a temperature of approximately 150° Celsius (+/−5°) for approximately 15 minutes (+/−5 minutes) to heat set tube 161 in the twisted configuration. According to an alternate embodiment, tube 161 is extruded or molded into the illustrated configuration without need for such a secondary process.

Figure 3A:
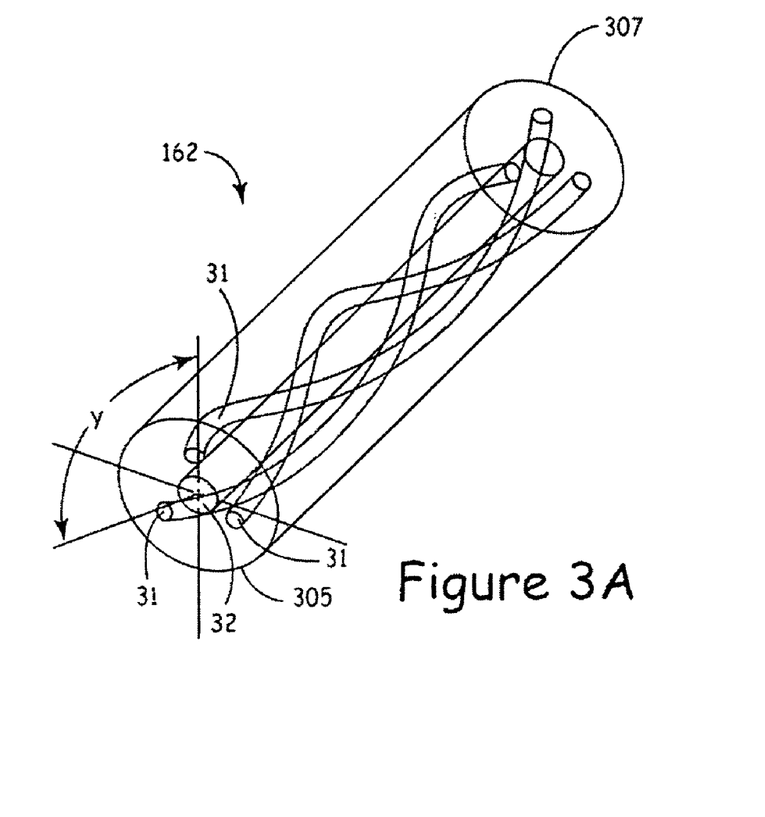
Figure 3B:
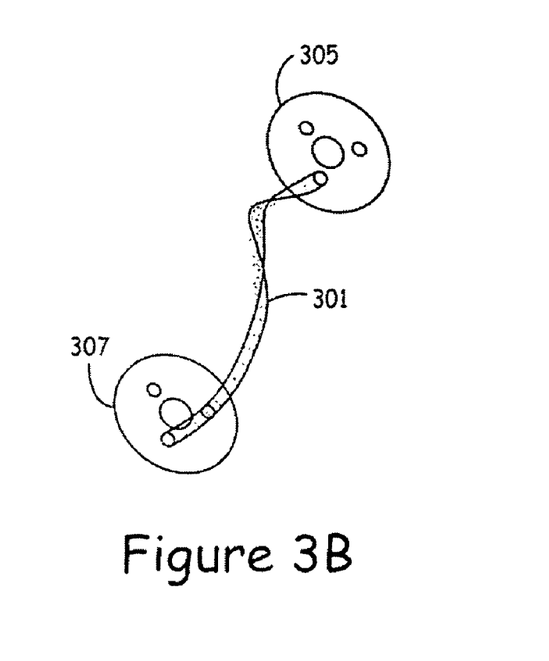

FIGS. 3A-B are a perspective view and schematic, respectively, of second multi-lumen tube 162 according to some embodiments of the present invention. FIGS. 3A-B illustrate tube 162 including a central lumen 32 and three peripheral lumens 31 each extending from a first end 305 to a second end 307 of tube 162; peripheral lumens 31 each extend along a helical path about central lumen 32, a trajectory of which may be seen in FIGS. 3A-B, more clearly illustrated in FIG. 3B by path 301. According to the illustrated embodiment, peripheral lumens 31 twist about central lumen 32 from first end 305 to second end 307 in an angle, which is approximately 360 degrees, but may be as great as approximately 400 degrees; a length of tube 162 from first end 305 to second end 307 is between approximately 0.5 inch and 1 inch.

According to an exemplary embodiment of the present invention, second multi-lumen tube 162 is made of silicone which may either have been extruded or molded into the twisted configuration illustrated in FIGS. 3A-B. According to an alternate embodiment, second tube 162 may have been extruded from polyurethane and set in the twisted configuration via the process previously described for first tube 161.

Figure 4A:
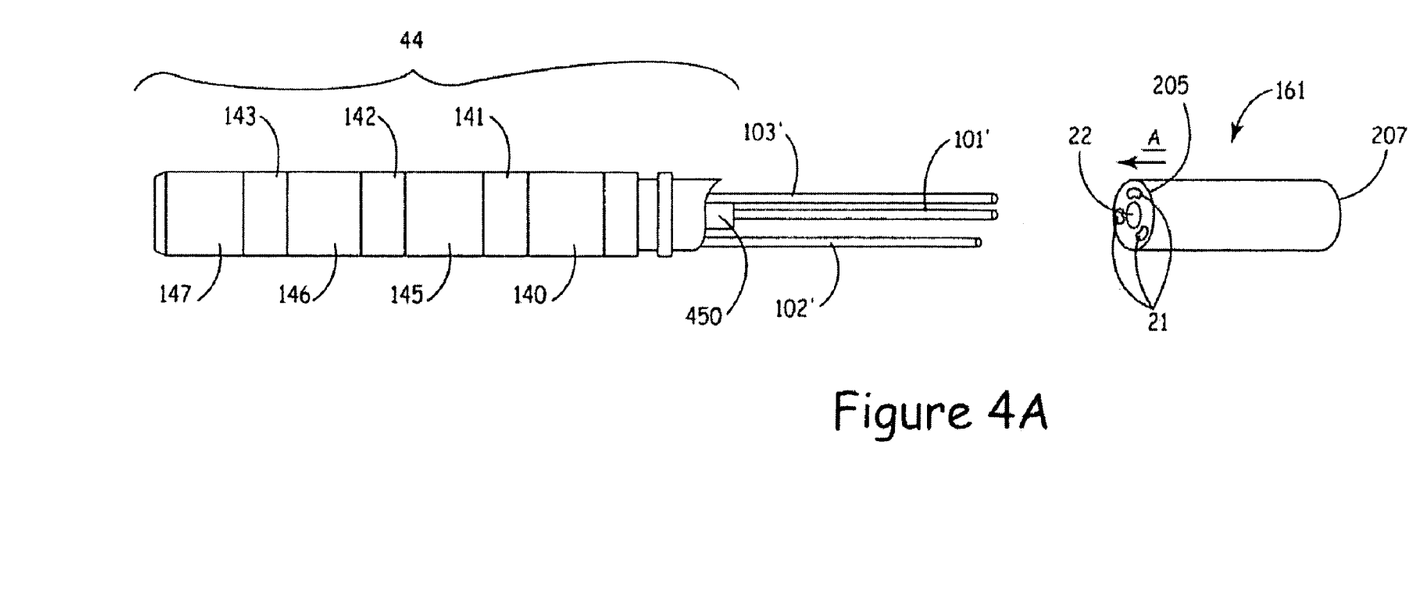
FIGS. 4A-B are plan views illustrating assembly steps according to some methods of the present invention.
Figure 4B:
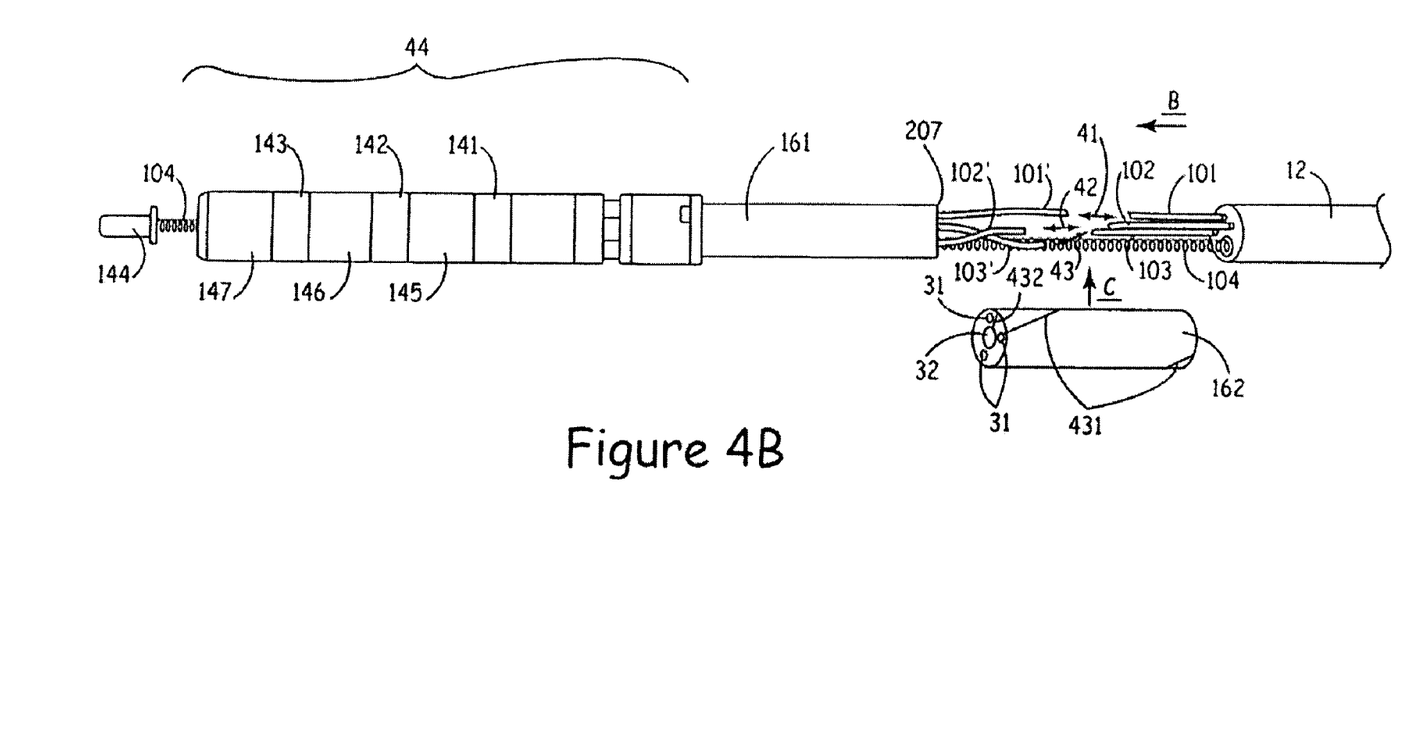

FIGS. 4A-B are plan views illustrating assembly steps according to some methods of the present invention. FIG. 4A illustrates a partial connector assembly 44 wherein connector contacts 141, 142 and 143 are mounted on an internal strut, whose distal end 450 is shown; contacts 141, 142 and 143 are each coupled to conductors 101', 102' and 103', respectively, shown extending from a distal end of assembly 44, and alternate with insulative spacers 140, 145, 146 and 147, which are also mounted on the strut. Such a connector assembly is described in co-pending and commonly assigned patent application Ser. No. 10/812,796 (Attorney Docket P-11476.00), which is incorporated by reference in its entirety herein.

According to one method of the present invention illustrated in FIG. 4A, an initial transition zone assembly step includes positioning first multi-lumen tube 161 adjacent connector assembly 44 per arrow A while inserting each of conductors 101', 102' and 103' into a respective peripheral lumen 21 of first tube 161; first end 205 of tube 161 is coupled to connector assembly 44 by inserting strut distal end 450 into central lumen 22 according to one embodiment. Once first tube 161 is positioned, distal ends of conductors 101', 102' and 103' extend distally from second end 207 of tube 161 as illustrated in FIG. 4B.

According to the embodiments described in conjunction with FIGS. 2A-B, a polyurethane material forming first tube 161, preferably having a hardness or durometer of about 55 on a Shore D scale, the length of first tube 161, and the twist, according to angle T, of peripheral lumens 21 can all facilitate insertion of each of conductors 101', 102' and 103' into respective lumens 21 without kinking of conductors 101', 102' and 103'. Furthermore, according to these embodiments, the polyurethane lends a stiffness to transition zone 10 that can facilitate insertion of connector 14 (FIG. 1) into a device connector bore when transition zone 16 is grasped for such insertion.

FIG. 4B illustrates a series of steps subsequent to that illustrated in FIG. 4A, according to some methods of the present invention. According to the illustrated embodiment, lead body 12, having conductors 101, 102, 103 and 104 extending proximally therefrom, is positioned in proximity to first tube 161, having conductors 101', 102' and 103' extending distally therefrom, and is advanced per arrow B such that conductor 104 is inserted through central lumen 22 of first tube 161 and through connector assembly 44. As illustrated in FIG. 4B, proximal ends of conductors 101, 102 and 103 and distal ends of conductors 101', 102' and 103' are brought together per arrows 41, 42 and 43, respectively to form splice junctions 111, 112 and 113 (FIG. 1), while a proximal end of conductor 104 is extended from a proximal end of connector assembly 44 to be coupled with connector contact pin 144. Splice junctions 111, 112 and 113 may be formed with or without additional components using methods, for example welding and crimping, known to those skilled in the art.

FIG. 4B further illustrates second multi-lumen tube 162 directed per arrow C in order to position second tube 162 between first tube 161 and lead body 12 and to position conductor 104 within central lumen 32 and each conductors 101/101', 102/102' and 103/103' within respective peripheral lumens 31. According to the illustrated embodiment, a slit 432 extending from an exterior surface of second tube 162 to central lumen 32 allows for positioning, per arrow C, of conductor 104 within central lumen 32, and slits 431 extending from the exterior surface to peripheral lumens 31 likewise allow positioning of conductors 101/101', 102/102' and 103/103' within peripheral lumens 31. Splice junctions 111, 112 and 113 may be formed either before or after positioning of second tube 162.

According to embodiments described in conjunction with FIGS. 3A-B, the shorter pitch of the helical path taken by peripheral lumens 31, of second tube 162, than the pitch of the helical path of peripheral lumens 21, of first tube 161, provide enhanced strain relief to the transition of conductors 101/101', 102/102' and 103/103'; furthermore the softer silicone material, preferably having a hardness or durometer of about 50-60 on a shore A scale, facilitates the slitting of tube 162 and positioning of conductors 101/101', 102/102', 103/103' and 104 according to the illustrated assembly method.

Figure 4C:
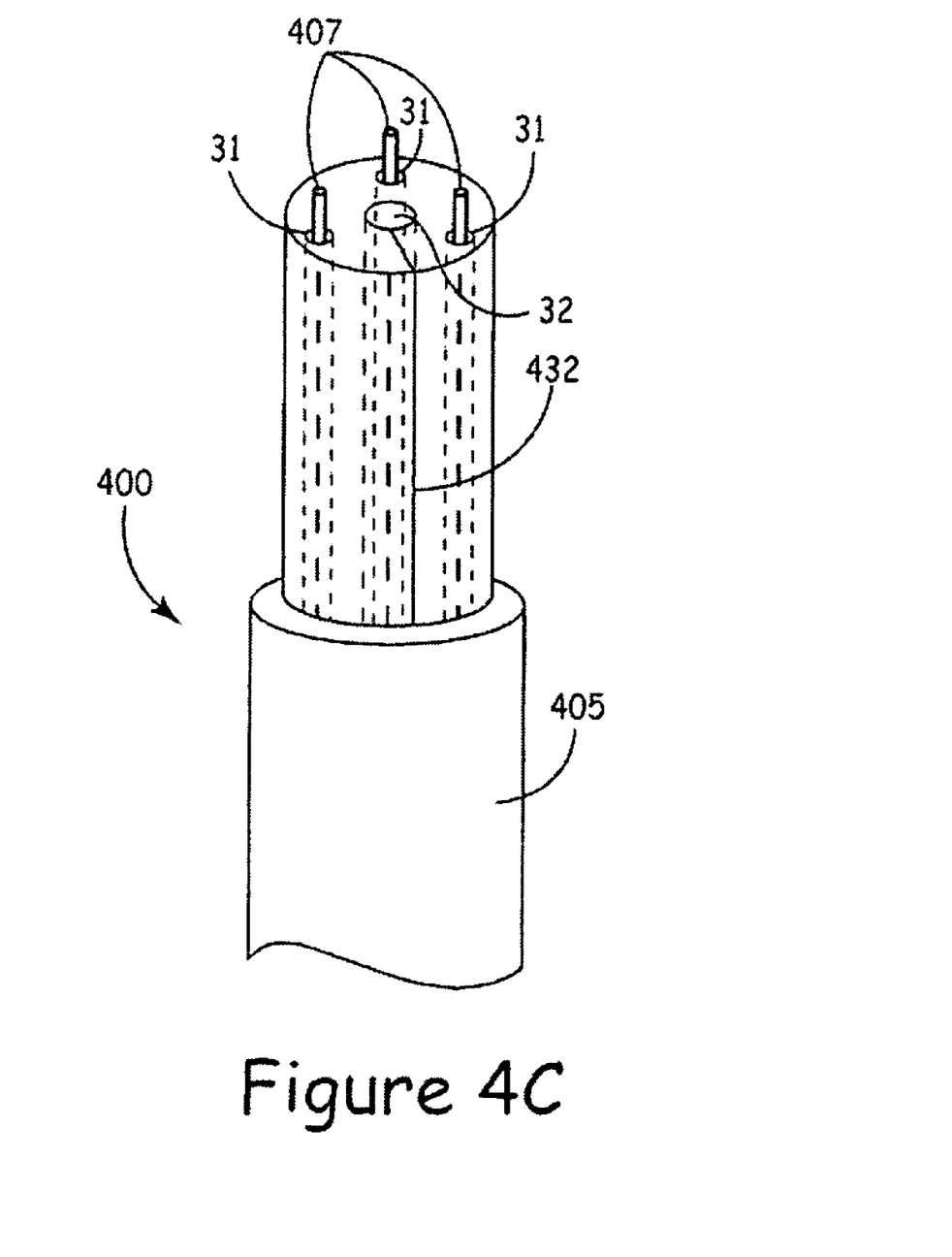
FIG. 4C is a perspective view according to one method of the present invention.

FIG. 4C is a perspective view according to one method of the present invention wherein a straightening fixture 400 is employed for forming slit 432 in second multi-lumen tube 162. FIG. 4C illustrates second tube 162 mounted on straightening fixture 400 such that each of mandrels 401 extending from a base 405 of fixture 400 are inserted within a respective peripheral lumen 31; mandrels 401 thus straighten peripheral lumens 31 so that slit 432 may be formed, for example with a cutting blade, without undue risk of cutting into peripheral lumens 31.

Returning now to FIG. 1, a final assembly step according to one method of the present invention includes positioning connector sleeve 160 to couple lead body 12 to connector terminal 14 and to encompass conductors 101/101', 102/102', 103/103' and 104 passing through transition zone 16. A silicone medical adhesive may be injected beneath connector sleeve 160 to fill in voids within transition zone 16; when both connector sleeve 160 and second multi-lumen tube 162 are formed of silicone, the silicone adhesive provides very good isolation of conductors 101/101', 102/102', 103/103' and 104 via a common material adhesion between adhesive, tube 162 and sleeve 160. Embodiments incorporating silicone adhesive backfill and silicone forming connector sleeve 160 and second tubing 162 also give transition zone 16 a flexibility facilitating bending of transition zone 16, distal to a point where zone 16 exits a device connector bore, when connector 14 is fully inserted in the bore and the proximal portion of lead body 12 is wrapped about the device according to methods known to those skilled in the art.

In the foregoing detailed description, the invention has been described with reference to specific embodiments. However, it may be appreciated that various modifications and changes can be made without departing from the scope of the invention as set forth in the appended claims. For example, although peripheral lumens of multi-lumen tubes have been illustrated as generally closed with respect to outer longitudinal surfaces of the tubes, tubes having peripheral lumens formed as open channels or grooves to route conductors are within the scope of the present invention and the term 'lumen' used herein is intended to broadly cover such a configuration.

What is claimed is:

1. A method for assembling a transition zone between a medical electrical lead body and a lead connector assembly, the method comprising the steps of:
   forming a multi-lumen tube having a peripheral lumen extending from a first end to a second end of the tube in a helical path about a central lumen of the tube;
   positioning the multi-lumen tube adjacent the connector assembly; and
   positioning a medical electrical lead conductor within the peripheral lumen by inserting an end of the medical electrical lead conductor into the first end of the peripheral lumen and advancing the end of the medical electrical lead conductor through the peripheral lumen;
   wherein the multi-lumen tube is formed of a polyurethane material and the step of forming the multi-lumen tube comprises:
   molding or extruding the tube such that the peripheral lumen extends from the first end to the second end approximately aligned with a central axis of the central lumen;
   twisting the first end of the tube with respect to the second end of the tube such that the peripheral lumen extends in the helical path;
   securing the first end and the second end in the twisted configuration; and
   heating the multi-lumen tube while the multi-lumen tube is in the twisted configuration.

2. A method for assembling a transition zone between a medical electrical lead body and a lead connector assembly, the method comprising the steps of:
   forming a multi-lumen tube having a peripheral lumen extending from a first end to a second end of the tube in a helical path about a central lumen of the tube;
   positioning the multi-lumen tube adjacent the connector assembly; and
   positioning a medical electrical lead conductor within the peripheral lumen by inserting an end of the medical electrical lead conductor into the first end of the peripheral lumen and advancing the end of the medical electrical lead conductor through the peripheral lumen;
   wherein the conductor has been coupled to the connector assembly before inserting the conductor into the first end of the peripheral lumen.

3. A method for assembling a transition zone between a medical electrical lead body and a lead connector assembly, the method comprising the steps of:
   forming a multi-lumen tube having a peripheral lumen extending from a first end to a second end of the tube in a helical path about a central lumen of the tube;
   positioning the multi-lumen tube adjacent the connector assembly; and
   positioning a medical electrical lead conductor within the peripheral lumen by inserting an end of the medical electrical lead conductor into the first end of the peripheral lumen and advancing the end of the medical electrical lead conductor through the peripheral lumen;
   wherein the conductor has been coupled to the lead body before inserting the conductor into the peripheral lumen.

4. A method for assembling a transition zone between a medical electrical lead body and a lead connector assembly, the method comprising the steps of:
   forming a multi-lumen tube having a peripheral lumen extending from a first end to a second end of the tube in a helical path about a central lumen of the tube;
   positioning the multi-lumen tube adjacent the connector assembly; and
   positioning a medical electrical lead conductor within the peripheral lumen by inserting an end of the medical electrical lead conductor into the first end of the peripheral lumen and advancing the end of the medical electrical lead conductor through the peripheral lumen; and
   further comprising the step of forming the conductor from a first conductor, which is coupled to the lead body, and a second conductor, which is coupled to the connector assembly, by splicing a proximal end of the first conductor, which extends proximally from the lead body, to a distal end of the second conductor, which extends distally from the connector assembly.

5. A method for assembling a transition zone between a medical electrical lead body and a lead connector assembly, the method comprising the steps of:
   forming a multi-lumen tube having a peripheral lumen extending from a first end to a second end of the tube in a helical path about a central lumen of the tube;
   positioning the multi-lumen tube adjacent the connector assembly; and
   positioning a medical electrical lead conductor within the peripheral lumen by inserting an end of the medical electrical lead conductor into the first end of the peripheral lumen and advancing the end of the medical electrical lead conductor through the peripheral lumen; and
   further comprising the step of positioning a second medical electrical lead conductor within the central lumen of the multi-lumen tube.

6. The method of claim 5, wherein the second medical electrical lead conductor is coupled to the lead body and extends proximally therefrom.

7. The method of claim 5, wherein the second conductor has been coupled to the connector assembly and the step of positioning the second conductor comprises inserting the second conductor into the first end of the central lumen.

8. The method of claim 5, wherein the second conductor has been coupled to the lead body and the step of positioning the second conductor comprises inserting the second conductor into the distal end of the central lumen.

9. The method of claim 5, wherein the step of positioning the second conductor comprises pressing the conductor from a longitudinal exterior surface of the tube into the central lumen.

10. The method of claim 2, further comprising the step of coupling a distal end of the conductor, which extends distally from the peripheral lumen of the multi-lumen tube, to another conductor extending proximally from the lead body to form a conductor splice.

11. The method of claim 2, further comprising the steps of;
forming a second multi-lumen tube having a second peripheral lumen extending from a first end of the second tube to a second end of the second tube in a helical path about a central lumen of the second tube;
positioning the second tube between the multi-lumen tube and the lead body; and
positioning the conductor within the second peripheral lumen.

12. The method of claim 11, wherein the step of positioning the conductor comprises pressing the conductor from a longitudinal exterior surface of the second tube into the second peripheral lumen.

13. The method of claim 6, further comprising the steps of:
forming a second multi-lumen tube having a second peripheral lumen extending from a first end of the second tube to a second end of the second tube in a helical path about a central lumen of the second tube;
positioning the second tube between the multi-lumen tube and the lead body; and
positioning the conductor within the second peripheral lumen.

14. The method of claim 13, further comprising the step of positioning the second conductor within the central lumen of the second tube.

15. The method of claim 14, wherein the step of positioning the second conductor comprises pressing the second conductor from a longitudinal exterior surface of the second tube into the central lumen.

16. The method of claim 10, further comprising the steps of:
forming a second multi-lumen tube having a second peripheral lumen extending from a first end of the second tube to a second end of the second tube in a helical path about a central lumen of the second tube;
positioning the second tube between the multi-lumen tube and the lead body; and
positioning the conductor splice within the second peripheral lumen.

17. The method of claim 16, wherein the step of positioning the splice of the conductors comprises pressing the splice from a longitudinal exterior surface of the second tube into the second peripheral lumen.

18. The method of claim 1, wherein the pitch of the internal peripheral lumen along at least a portion of the helical path is variable.

19. A method for assembling a transition zone between a medical electrical lead body and a lead connector assembly, the method comprising:
forming a multi-lumen tube having a peripheral lumen extending from a first end to a second end of the tube in a helical path about a central lumen of the tube, wherein the multi-lumen tube is formed of a polyurethane material and the forming comprises:
molding or extruding the tube such that the peripheral lumen extends from the first end to the second end approximately aligned with a central axis of the central lumen;
twisting the first end of the tube with respect to the second end of the tube such that the peripheral lumen extends in the helical path;
securing the first end and the second end in the twisted configuration; and
heating the multi-lumen tube while the multi-lumen tube is in the twisted configuration;
positioning the multi-lumen tube adjacent the connector assembly; and
positioning a medical electrical lead conductor within the peripheral lumen.

20. The method of claim 19, wherein positioning the medical electrical lead conductor within the peripheral lumen comprises inserting an end of the medical electrical lead conductor into the first end of the peripheral lumen and advancing the end of the medical electrical lead conductor through the peripheral lumen.

21. The method of claim 19, wherein positioning the medical electrical lead conductor within the peripheral lumen comprises pressing the conductor from a longitudinal exterior surface of the tube into the peripheral lumen.

22. A method for assembling a transition zone between a medical electrical lead body and a lead connector assembly, the method comprising:
forming a multi-lumen tube having a peripheral lumen extending from a first end to a second end of the tube in a helical path about a central lumen of the tube;
positioning the multi-lumen tube adjacent the connector assembly;
positioning a medical electrical lead conductor within the peripheral lumen; and
forming the medical electrical lead conductor from a first conductor, which is coupled to the lead body, and a second conductor, which is coupled to the connector assembly, by splicing a proximal end of the first conductor, which extends proximally from the lead body, to a distal end of the second conductor, which extends distally from the connector assembly.

23. The method of claim 22, wherein positioning the medical electrical lead conductor within the peripheral lumen comprises pressing the spliced portion of the conductor from a longitudinal exterior surface of the tube into the peripheral lumen.

24. A method for assembling a transition zone between a medical electrical lead body and a lead connector assembly, the method comprising:
forming a multi-lumen tube having a peripheral lumen extending from a first end to a second end of the tube in a helical path about a central lumen of the tube;
positioning the multi-lumen tube adjacent the connector assembly;
positioning a medical electrical lead conductor within the peripheral lumen; and
positioning a second medical electrical lead conductor within the central lumen of the multi-lumen tube.

25. The method of claim 24, wherein the second medical electrical lead conductor is coupled to the lead body and extends proximally therefrom.

26. The method of claim 25,wherein the method further comprises:
forming a second multi-lumen tube having a second peripheral lumen extending from a first end of the second tube to a second end of the second tube in a helical path about a central lumen of the second tube;
positioning the second tube between the multi-lumen tube and the lead body; and positioning the conductor within the second peripheral lumen.

27. The method of claim 26, further comprising positioning the second conductor within the central lumen of the second tube.

28. The method of claim 26, wherein positioning the second conductor comprises pressing the second conductor from a longitudinal exterior surface of the second tube into the central lumen.

29. The method of claim 24, wherein the second medical electrical lead conductor has been coupled to the connector assembly and positioning the second conductor comprises inserting the second conductor into the first end of the central lumen.

30. The method of claim 24, wherein the second conductor has been coupled to the lead body and positioning the second conductor comprises inserting the second conductor into the distal end of the central lumen.

31. The method of claim 24, wherein positioning the second conductor comprises pressing the conductor from a longitudinal exterior surface of the tube into the central lumen.

* * * * *